United States Patent
Cull et al.

(10) Patent No.: US 6,719,011 B2
(45) Date of Patent: Apr. 13, 2004

(54) TURBINE FLUID FLOW RESISTOR

(75) Inventors: Laurence J. Cull, Wildwood, MI (US); James T. Perkins, St. Charles, MI (US); Matthew J. Fitzgerald, St. Louis, MI (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/188,132

(22) Filed: Jul. 1, 2002

(65) Prior Publication Data

US 2004/0000349 A1 Jan. 1, 2004

(51) Int. Cl.$^7$ .............................. F15D 1/02; A61B 17/20
(52) U.S. Cl. .............................. 138/37; 138/39; 604/118
(58) Field of Search .............................. 138/37, 39, 42; 604/317, 319, 118, 119; 73/861.92

(56) References Cited

U.S. PATENT DOCUMENTS

| | | | | |
|---|---|---|---|---|
| 1,001,722 A | * | 8/1911 | Wilcox et al. | 73/861.92 |
| 2,270,141 A | * | 1/1942 | Potter | 290/52 |
| 3,119,263 A | * | 1/1964 | Perkins | 73/861.92 |
| 3,217,539 A | * | 11/1965 | Owen et al. | 73/861.77 |
| 3,433,071 A | * | 3/1969 | Homrig | 73/861.92 |
| 3,543,579 A | * | 12/1970 | Watkins | 73/861.92 |
| 3,948,099 A | * | 4/1976 | Geisow | 73/861.92 |
| 4,189,941 A | * | 2/1980 | Loesch | 73/861.79 |
| 4,316,392 A | * | 2/1982 | Leber | 73/861.83 |
| 4,395,919 A | * | 8/1983 | Peters | 73/861.77 |
| 4,700,579 A | * | 10/1987 | Hall | 73/861.78 |
| 4,921,477 A | * | 5/1990 | Davis | 604/22 |
| 5,106,367 A | * | 4/1992 | Ureche et al. | 604/30 |

* cited by examiner

*Primary Examiner*—Patrick Brinson
(74) *Attorney, Agent, or Firm*—Michael L. Smith

(57) ABSTRACT

A fluid flow resistor 10 for use in ophthalmic surgery includes a housing 12 having an inlet 14 and an outlet 16. An elongated turbine 22 is caused to spin within the housing 12 by a flow of fluid which extracts energy from the fluid flow and effectively increases a resistance to fluid flow from the inlet 14 to the outlet 16.

4 Claims, 1 Drawing Sheet

TURBINE FLUID FLOW RESISTOR

BACKGROUND OF THE INVENTION

1. Field of the Invention

The present invention is related to devices for controlling aspirant fluid flow during ophthalmic surgery. More particularly, the present invention is directed to an aspirant fluid flow resistor for increasing the resistance to fluid flow in an aspiration path during ophthalmic surgery.

2. Description of Related Art

During eye surgery, especially cataract surgery, surgeons experience a tension between the amount of vacuum or aspiration to be used on a patient's eye and the time period in which the surgeon has to respond to events that may occur during surgery. Surgeons typically prefer higher vacuum levels to provide a higher holding force for the cataract. However, these higher vacuum levels result in the need for rapid response times by the surgeon when events such as occlusion occur in the aspiration line. The higher the vacuum levels, the quicker events occur and thus the potential for serious problems increases, such as the tearing of the capsular bag.

There are known devices for increasing the resistance to aspirant fluid flow to allow a surgeon to use higher vacuum levels, i.e., higher holding force, with a slower response time. These devices help the surgeon have the benefits of higher vacuum levels while limiting or minimizing the risks by providing the surgeon with greater time to respond to surgical events than would be possible without resistance to the aspirant flow. Coiled tubing is one example that increases the flow resistance. It has been asserted that increased resistance is achieved by passing fluid through a series of coil bends because fluid drops in pressure as it flows through a bend. However, a downside to the coiled tubing is that the chances of aspirant clogging within the coils is increased due to the elliptical cross-section and bent kinks that may occur in the tubing. In addition, the resistance of the coiled tubing is a function of the coil radius.

Another device that increases resistance to aspirant flow is a non-clogging orifice that collects waste and is commonly referred to phaco-guard. The phaco-guard is a large cross-sectional area filter funneled down to a small orifice. It allows limited clogging of the filter and is based on the assumption that the entire filter area will not clog. However, the filter may still clog.

Therefore, it would be desirable to have a compact, easily manufactured fluid flow resistor for increasing resistance to fluid flow and an aspiration path.

DETAILED DESCRIPTION OF THE PREFERRED EMBODIMENT

Figure 1:
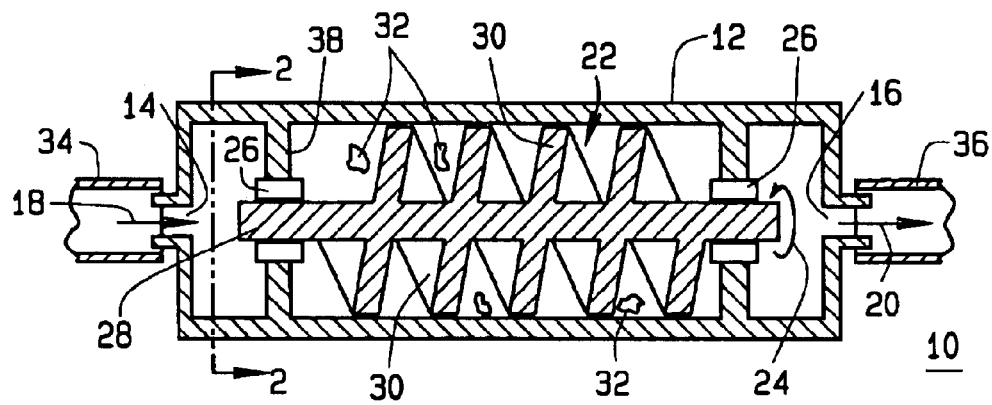
FIG. 1 is a cut-away elevation of a fluid flow resistor in accordance with the present invention.

A fluid flow resistor 10 for use in ophthalmic surgery is shown in FIG. 1. Resistor 10 includes a housing 12, including an inlet 14 and an outlet 16 for receiving a flow of fluid within the housing along a path indicated by arrows 18 and 20. An elongated turbine 22 is disposed within the housing 12, such that a flow of fluid from the inlet 14 will cause the turbine 22 to spin as indicated by arrow 24.

The spinning of turbine 22 extracts energy from the fluid flow and effectively increases a resistance to the fluid flow from the inlet 14 to the outlet 16.

Preferably, the resistor 10 includes bearings 26 between the housing 12 and the turbine 22 for allowing the turbine to spin with a minimal, frictional resistance. It is preferred that turbine 22 be allowed to spin as freely as possible in order to extract as much energy as possible. However, it will be appreciated that the frictional forces on center shaft 28 about which thread 30 is formed will be a factor in the velocity at which turbine 22 spins and therefore, effect the amount of energy extracted from the fluid flow within housing 12. The more easily turbine 22 spins, the more energy that will be extracted from the fluid flow within housing 12, resulting in an increased resistance to fluid flow.

During ophthalmic surgery, the fluid flow will contain particles, such as pieces of cataract 32 and it is preferred that each turn of thread 30 be spaced along the center shaft 28 a sufficient distance to allow the aspirant particles 32 to flow from the inlet 14 to the outlet 16 without becoming clogged.

FIG. 1 shows surgical tubing 34 which forms an aspiration line from the surgical handpiece conducting the surgery on the eye (not shown) to the inlet 14. Tubing 36 attached to outlet 16 is typically connected to a standard fluid collection cassette (not shown) well known in the art, such as those available for use with Bausch & Lomb's Millennium™ Surgical System.

Figure 2:
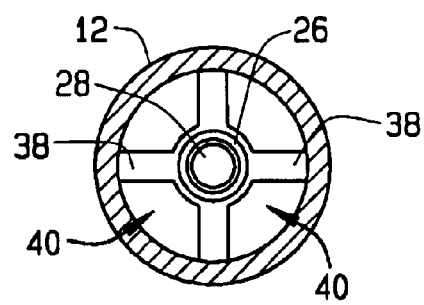
FIG. 2 is a cut-away front elevation of a fluid flow resistor in accordance with the present invention taken along lines 2—2 of FIG. 1.

FIG. 2 shows housing 12, which holds turbine 22 with support members 38, supporting bearing 26 and center shaft 28. Obviously, spaces 40 should be large enough to allow fluid and particles 32 to flow freely past support members 38.

In practice during ophthalmic surgery, the greater the vacuum level at the surgical site the more work that can be done by surgical instruments, such as a phaco handpiece for breaking up and removing cataracts from a patient's eye. However, this increased vacuum can lead to certain dangers during eye surgery if the aspiration path becomes occluded, particularly immediately following the removal of the occlusion. Such dangers include collapsing the capsular bag in the eye, tearing the capsular bag, or other trauma to the eye. The greater the vacuum level the more immediate and greater the potential damage that can be done to the eye, and the quicker the surgeon needs to react to the removal of the occlusion. This tension between the benefits of a higher vacuum level and the pace at which events occur causes some surgeons to perform surgery at lower vacuum levels to avoid the possible complications of higher vacuum. To minimize the trade-off, the present invention allows high vacuum levels to be used because of the increased resistance introduced into the aspiration line than otherwise would be available with a standard length of tubing connected to a fluid collection cassette. By introducing this increased fluid flow resistance, higher vacuum levels can be used by the surgeon without fear that any aspirational occlusion will cause a problem that could not be handled by the surgeon.

As those familiar with fluid flow are well aware, Bernoulli's equation includes factors, such as fluid flow loss due to friction, fluid flow velocity loss due to energy being extracted, and fluid flow gain by the introduction of energy to the flow path. Typically in ophthalmic surgery, losses due to friction and energy extraction are considered to approach 0. In the present invention however, energy can be extracted from the fluid flow path by the spinning of the turbine 22 and by the friction between the turbine shaft 28 and any bearing surface 26. These factors in Bernoulli's equation removing energy from the fluid flow path effectively increases the fluid flow path length, which directly results in an increase in the fluid flow resistance of the fluid flow path or aspiration path.

Figure 3:
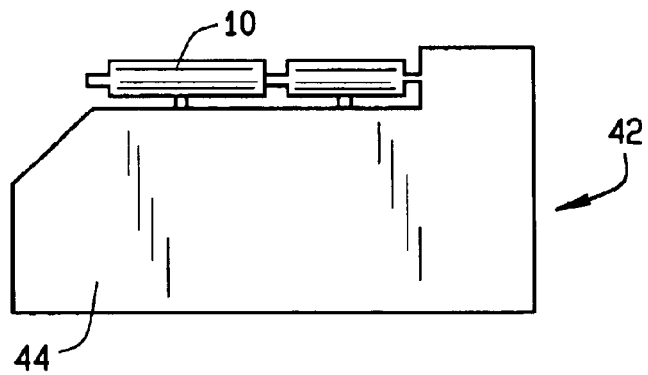
FIG. 3 is a side elevation of an aspirant fluid collection cassette in accordance with the present invention.

FIG. 3 shows a turbine resistor 10 as described above in FIG. 1 integrally formed with a fluid collection cassette 42 for receiving and collecting aspirant fluid from a surgical site in reservoir 44. Cassette 42 is otherwise preferably constructed as other well-known prior art fluid collection cassettes for use in ophthalmic surgery.

Thus, there has been shown a turbine fluid flow resistor for extracting energy from the fluid flow path and effectively increasing resistance to fluid flow.

We claim:

1. A fluid flow resistor cassette for use in ophthalmic surgery comprising:

an aspirant fluid collection cassette for receiving and collecting aspirant fluid from a surgical site in a reservoir;

a housing integrally formed with the cassette, such that the housing includes an inlet for receiving the aspirant fluid and an outlet in communication with the reservoir; and an elongated turbine disposed within the housing, such that a flow of aspirant fluid from the inlet will cause the turbine to spin, thereby extracting energy from the fluid flow and effectively increasing a resistance to the fluid flow from the inlet to the outlet.

2. The resistor of claim 1 further includes a bearing between the housing and the turbine for allowing the turbine to spin with a minimal frictional resistance.

3. The resistor of claim 1 wherein the turbine includes an elongated center shaft about which a thread is formed.

4. The resistor of claim 1 wherein each turn of the thread is spaced along the center shaft a sufficient distance to allow aspirant particles to flow from the inlet to the outlet without becoming clogged.

* * * * *